United States Patent [19]

Guerrero

[11] Patent Number: 5,486,352
[45] Date of Patent: Jan. 23, 1996

[54] SUNSCREEN COMPOSITIONS

[75] Inventor: Angel A. Guerrero, Huntington, Conn.

[73] Assignee: Elizabeth Arden Company, New York, N.Y.

[21] Appl. No.: 367,650

[22] Filed: Jan. 3, 1995

[51] Int. Cl.$^6$ .................................................. A61K 7/42
[52] U.S. Cl. ........................... 424/59; 424/60; 514/937; 514/938
[58] Field of Search ..................... 424/59, 60; 514/937, 514/938

[56] References Cited

U.S. PATENT DOCUMENTS

| | | | |
|---|---|---|---|
| 4,919,934 | 4/1990 | Deckner et al. | 424/401 |
| 5,008,100 | 4/1991 | Zecchino et al. | 424/59 |
| 5,219,558 | 6/1993 | Woodin, Jr. et al. | 424/59 |
| 5,417,961 | 5/1995 | Nearn | 424/59 |

Primary Examiner—Ceila Chang
Assistant Examiner—Evelyn Huang
Attorney, Agent, or Firm—Milton L. Honig

[57] ABSTRACT

A cosmetic sunscreen composition is described that includes an emulsion formed from water, an emollient oil and an organic sunscreen agent capable of absorbing ultraviolet radiation within the range of 290 to 400 nm. Further included in the sunscreen composition is a microfluidized medium formulated and microfluidized separately and prior to blending with the other aforementioned components. This medium includes water, a phospholipid, and an organic sunscreen agent identical to that in the emulsion. The combination of identical sunscreen agents in different environments provides an overall increase in SPF for the overall sunscreen composition.

6 Claims, No Drawings

SUNSCREEN COMPOSITIONS

BACKGROUND OF THE INVENTION

1. Field of the Invention

The invention relates to sunscreen compositions, particularly those in lotion and cream form.

2. The Related Art

Sunscreen compositions are commonly used during outdoor work or leisure for protection of exposed skin against sunburn, cancer and even photo ageing. Many effective sunscreen preparations are sold commercially or are described in cosmetic or pharmaceutical literature. In general, sunscreen preparations are formulated as creams, lotions or oils containing as the active agent an ultraviolet radiation absorbing chemical compound. The active agent functions by blocking passage of erythematogenic radiation thereby preventing its penetration into the skin.

The ideal sunscreen formulation should be non-toxic and non-irritating to skin tissue and be capable of convenient application in a uniform continuous film. The product should be sufficiently chemically and physically stable so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water. For aesthetic reasons, the product should be substantially odorless (or be capable of being scented) and be non-staining to the skin or clothing.

Sunscreen agents in the order of decreasing effectiveness may be categorized as either highly chromophoric monomeric organic compounds, inorganic compounds and minimally chromophoric polymeric organic solids.

U.S. Pat. No. 5,219,558 (Woodin, Jr. et al.) and U.S. Pat. No. 4,919,934 (Deckner et al.) disclose photoprotection compositions wherein the active sunscreen agents are of the chromophoric monomeric organic compound variety. The examples feature the commercially common sunscreens such as octyl methoxycinnamate (Parsol MCX), benzophenone-3 (Oxybenzone) and octyl dimethyl PABA.

Chromophoric monomeric organic compounds are subject to certain problems. One of the more important problems is that of skin irritation. Some people are quite sensitive to organic molecules with chromophoric groups. Adverse allergic reactions can result. Incidentally, increasing the concentration of a sunscreen does not necessarily increase the SPF, and indeed has shown may decrease the protective factor. This negative response has been attributed by some to micelle interference with the sunscreen over concentration. Therefore, it would be quite desirable to minimize the level of such compounds in any sunscreen compositions. Total replacement of chromophoric organic compounds, while desirable, is presently not feasible for high SPF compositions that also require certain types of aesthetics.

Inorganic particulate compounds such as titanium dioxide have been employed as sunscreen agents. In fact, titanium dioxide is quite popular with marketers advertising them as "natural sunscreens". The problem with inorganic particulate compounds is that high SPF values can only be achieved with high concentrations of these materials. Unfortunately, aesthetics suffer at such high concentrations. Clear formulas become opaque. High loadings also tend to form visible white films on the skin which consumers perceive negatively.

Polymeric organic particulates are a final category of materials which have found use in sunscreen formulations. U.S. Pat. No 5,008,100 (Zecchino et al.) reports oil-in-water emulsions containing polyethylene particles as a co-active sunscreen agent along with the traditional chromophoric organic compounds. Similar to the inorganic materials, polymeric particles are limited in their sunscreen effectiveness. High amounts of such materials will have adverse effects upon the formula aesthetics.

Accordingly, it is an object of the present invention to provide a sunscreen composition that maximizes the sun protection factor but minimizes the level of chromophoric monomeric organic compound.

Another object of the present invention is to provide a sunscreen composition in the form of an oil and water emulsion that exhibits improved aesthetics when applied to the skin.

Yet another object of the present invention is to provide a sunscreen composition having a much lower human irritancy than formulas of equivalent sun protection factor.

These and other objects of the present invention will more readily become apparent from the description and examples which follow.

SUMMARY OF THE INVENTION

A sunscreen composition is provided which includes:

(i) from about 1 to about 90% by weight of water;
(ii) from about 1 to about 90% by weight of an emollient oil;
(iii) from about 0.1 to about 30% by weight of an organic sunscreen agent with a chromophoric group active within the ultraviolet radiation range from 290 to 400 nm; and
(iv) from about 0.1 to about 50% by weight of a microfluidized medium that includes:
   from about 1 to about 80% by weight of water;
   from about 0.001 to about 5% by weight of a phospholipid; and
   from about 1 to about 50% by weight of an organic sunscreen agent identical to that of component (iii), and the medium being formulated and microfluidized prior to blending with components (i) to (iii).

DETAILED DESCRIPTION OF THE INVENTION

Now it has been discovered that a microfluidized medium containing an organic sunscreen agent when blended into an emulsion containing further amounts of an identical organic sunscreen agent will provide to resultant compositions a significant boost in the sun protection factor (SPF). The organic sunscreen agent outside of the microfluidized medium will ordinarily be soluble in the emollient oil phase of the emulsion. Organic sunscreen agent trapped within the microfluidized medium will ordinarily be delivered via the medium to the water phase of the emulsion. As a consequence, the oil and water emulsion has identical organic sunscreen agent distributed both in the oil and the water phases. Much greater SPF efficiency is thereby achieved.

Accordingly, sunscreen compositions of the present invention will be emulsions containing an oil and a water phase. Water constituting the latter phase will be present in an amount from about 1 to about 90% by weight thereof. Preferably the level of water will range from about 30 to about 80%, optimally between about 50 and about 70% by weight.

Emollient materials will form the oil phase of emulsions according to the present invention. These emollient materials may be in the form of hydrocarbons, silicones, synthetic or natural esters and combinations thereof. Amounts of the emollient oil will range from about 1 to about 90%, preferably from about 10 to about 60%, optimally from about 15 to about 25% by weight.

Hydrocarbons may be in the form of mineral oil, terpenes (such as squalene), isoparaffins and petroleum jelly.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 344 and Dow Corning® 345.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Silicone copolyols are particularly useful as emollient and emulsifying materials within the context of the present invention. Particularly preferred is Dow Corning® 3225C fluid, a mixture of cyclomethicone and dimethicone copolyol having viscosity at 25° C. of 600–2000 cps and a specific gravity of about 0.963.

Among the ester emollients are:

(1) Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Mono-, Di- and Triglyceride esters such as PEG-8 caprylic/capric triglyceride.

(6) Sterols esters, of which cholesterol fatty acid esters are examples thereof.

Blended within the aforementioned emulsions of the present system will be an organic sunscreen agent having at least one chromophoric group absorbing within the ultraviolet range somewhere from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, αphenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy-or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-isopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |

TABLE I-continued

| CTFA NAME | TRADE NAME | SUPPLIER |
| --- | --- | --- |
| Glyceryl PABA | NIPA G.M.P.A. | Nipa Labs. |
| Homosalate | KEMESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 6300 | EM Industries |
| TEA salicylate | SUNAROME W | Felton Worldwide |
| 2-(4-Methylbenzlidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl Methoxy dibenzoyl methane | PARSOL 1789 | Givaudan Corp. |
| Etocrylene | UVINUL N-35 | BASF Chemcial Co. |

Amounts of the aforementioned sunscreen agents will generally range from about 0.1 to about 30%, preferably from about 2 to about 20%, optimally from about 4 to about 10% by weight.

Optionally there may be present in the sunscreen emulsion compositions of the present invention a variety of other materials. Examples include fatty acids, humectants, thickeners/viscosifiers, surfactants, preservatives, biologically active materials and other adjunct ingredients. These are described more fully below.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol (known also as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners/viscosifiers in amounts from about 0.01 to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B. F. Goodrich under the Carbopol trademark.

Surfactants may also be present in cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from about 2 to about 100 moles of ethylene oxide or propylene oxide per mole of hydrophobe; the $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates and combinations thereof.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.1 to about 9%, optimally between about 0.5 and about 7% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 115®), sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), ceramides (such as Ceramide I and Ceramide III), biohyaluronic acid (with oligosaccharides, available as Actiglide J® from Active Organics US) and sodium PCA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont. Another natural material is plant pseudocollagen commercially available from Brooks, Inc., South Plainfield, N.J.

Amounts of each of the foregoing materials may range from about 0.001 to about 10%, preferably from about 0.05 to about 1%, optimally between about 0.1 and 0.5% by weight.

Colorants, fragrances, opacifiers and abrasives may also be included in compositions of the present invention. Each of these substances may range from about 0.05 to about 5%, preferably between 0.1 and 3% by weight.

Besides the water and emollient oil components, sunscreen emulsion compositions of the present invention require the presence of a microfluidized medium component. The medium will contain water, a phospholipid, and an organic sunscreen agent identical to that within the water and emollient oil emulsion. The medium is formulated and microfluidized prior to blending with the water, emollient oil and first portion of the organic sunscreen agent.

Amounts of water in the microfluidized medium may range from about 1 to about 80%, preferably from about 30 to about 75%, optimally from about 65 to about 70% by weight of the medium. The amount of phospholipid may range from about 0.01 to about 5%, preferably from about 0.01 to about 2%, optimally from about 0.5 to about 1% by weight of the medium. The amount of organic sunscreen agent within the medium may range from about 1 to about 50%, preferably from about 5 to about 35%, optimally from about 12 to about 24% by weight of the medium.

A further material which can improve the stability of the microfluidized medium will be a silicone oil. Particularly effective will be a combination of dimethicone copolyol and cyclomethicone, commercially available as Dow Corning® 3225C. Amounts of the silicone oil may range from about 1 to about 30%, preferably from about 5 to about 20%, optimally between about 8 and 15% by weight of the medium.

Sunscreen cosmetic compositions of the present invention may be in any form. These forms may include creams, lotions, sticks, roll-on formulations, mousses, aerosol sprays and pad-applied formulations. Most preferred are creams and lotions.

As earlier noted, compositions of the present invention require a portion of the organic sunscreen to be suspended in a microfluidized medium. Microfluidization is a well-known processing technique. Microfluidization can be described as the dynamic interaction of two fluid streams in precisely defined microchannels resulting in the production of fine emulsions and dispersions with narrow size distribution. A fine emulsion is defined as one in which the droplet size of the dispersed phase is substantially below one micron, usually in the range of from 0.0001 to 0.8 micron, preferably from 0.01 to 0.5 micron.

The process may be conducted in an air-driven microfluidizer operating at pressures up to 10,000 psi. Feedstock can be premixed or the individual phases left separate and fed coaxially. Product may be continuously processed or recycled via a closed loop.

Intensity of fluid stream interactions and the resultant emulsion fineness is controllable by changes in interaction chamber configuration, pressure and number of passes.

The following Examples will more fully illustrate the embodiments of this invention. All parts, percentages and proportions referred to herein and in the appended claims are by weight unless otherwise indicated. These weight percentages relate to the total sunscreen composition (i.e. emulsion plus microfluidized medium) except where otherwise specified.

EXAMPLE 1

A series of experiments were conducted to evaluate the SPF contribution from sunscreen agents both outside and within a microfluidized medium. Table I sets forth the base composition of the fully formulated product, except without sunscreen.

In-vitro SPF of the formulated product, was measured with an SPF-290 Analyzer, manufactured by Optometrics USA, Inc. of Ayer, Mass.

The optical system of the SPF-290 is comprised of a continuous UV-VIS source, color compensating filters, diffusion plates, a grating monochromator and detector. Ultraviolet (UVB) and near ultra-violet (UVA) radiation is provided by a Xenon arc lamp. The radiation emitted from the source is attenuated in such a way that it more closely resembles the solar spectrum. The beam of radiation reaches the sample and, at that point, is either transmitted, absorbed or reflected by the sample or substrate. Transmitted radiation passes through a series of diffuser plates which further attenuate it. Then the beam enters a monochromator and, ultimately, the monochromatic radiation impinges on the photosensitive surface of the detector, generating a signal that is proportional to the intensity of the radiation striking the surface.

The method of measurement involved applying 80 microliters of sample onto a Vitro-Skin® substrate (commercially available from Innovative Measurement Solutions, Inc.) supported by a holder. The sample was applied to an area of 6.4×6.4 cm² in such a manner that a surface was covered approximating 40 cm². An amount of sample equal to 2 microliters per cm², which is similar to that used in standard in-vivo SPF tests, was distributed on the test substrate. SPF measurements were then taken on the sample formulas.

TABLE I

| BASE COMPOSITION | |
|---|---|
| COMPONENT | WEIGHT % |
| Potassium Lactate | 10.0000 |
| Silicone Fluid 344 | 6.1000 |
| Octyl Methoxycinnamate | 4.0000 |
| Potassium Hydroxide (45% Soln.) | 3.0000 |
| $C_{12}$–$C_{15}$ Alkyl Benzoate | 2.9000 |
| Dimethicone Copolyol | 2.3000 |
| Propylene Glycol | 2.0000 |
| Glycerin | 2.0000 |
| Octyl Stearate | 1.2000 |
| Octyl Dodecyl Neopentanoate | 1.1000 |
| Cetyl Dimethicone | 0.6500 |
| Silicone Fluid 200 (10 cst) | 0.4500 |
| Polyglyceryl-2 Beeswax | 0.4000 |
| Dimethicone Copolyol Beeswax | 0.4000 |
| Urea | 0.2500 |
| Squalene | 0.2000 |
| Polyglyceryl Ricinoleate | 0.2000 |
| Saccharide Isomerate | 0.2000 |
| Sodium PCA | 0.2000 |

TABLE I-continued

| BASE COMPOSITION | |
|---|---|
| COMPONENT | WEIGHT % |
| Propylparaben | 0.1000 |
| Methylparaben | 0.1000 |
| Disodium EDTA | 0.1000 |
| Ceramide | 0.0011 |
| Deionized Water | to 100 |

Under Table II there are reported the SPF of the base emulsion and of variations of the base composition with Parsol MCX (octyl methoxycinnamate).

TABLE II

| SUNSCREEN COMPONENTS | A | B | C | D | E |
|---|---|---|---|---|---|
| Parsol MCX (within Base Emulsion but external of Microfluidized Medium) | 4 | 5.12 | 4.00 | 0 | 0 |
| Parsol MCX (within Microfluidized Medium) | 0 | 0 | 1.12 | 1.12 | 0 |
| None (Base Emulsion) | 96 | 94.88 | 94.88 | 98.88 | 100 |

TABLE III

| SUNSCREEN ACTIVITY | A | B | C | D | E |
|---|---|---|---|---|---|
| SPF | 14.7 | 13.1 | 17.1 | 6.3 | 1.1 |

Formula A demonstrates that Parsol MCX® in the water and emollient oil emulsion provides an SPF of 14.7 as compared to Formula E without any sunscreen with an SPF of 1.1. A slight increase of the sunscreen agent to 5.12% in Formula B provided an SPF of 13.1. When the extra 1.12% Parsol MCX® carried within the microfluidized medium was dosed to the base emulsion, the SPF rose to 17.1. Formula D which includes only 1.12% Parsol MCX® as delivered via the microfluidized medium displayed an exceptionally high SPF of 6.3. From these results it is seen that the combination of a sunscreen agent having a portion within the base emulsion and a another portion within the microfluidized medium can result in an overall composition of higher than expected SPF value.

EXAMPLE 2

A series of cream sunscreen type compositions according to the present invention are described below.

TABLE IV

| COMPONENTS | A | B | C | D | E | F |
|---|---|---|---|---|---|---|
| Dow Corning 3225® | 14.00 | 14.00 | 14.00 | 20.00 | 18.00 | 18.00 |
| Microfluidized Medium* | 9.00 | 12.00 | 16.00 | 16.00 | 7.50 | 7.50 |
| Aluminum Stearate Gel 4** | 4.00 | 4.00 | 4.00 | 4.00 | 4.00 | 4.00 |
| Parsol MCX ® | 3.00 | 3.00 | 6.00 | 2.00 | 3.00 | 3.00 |
| Sodium Chloride | 3.00 | 3.00 | 3.00 | 3.00 | 3.00 | 3.00 |
| Butylene Glycol | 2.50 | 2.50 | 2.50 | 2.50 | 2.50 | 2.50 |
| Actiglide J ® | 2.20 | 2.20 | 2.20 | 2.20 | 2.20 | 2.20 |
| Glycerin | 1.50 | 1.50 | 1.50 | 1.50 | 1.50 | 1.50 |
| Sodium Lactate (in water) | 1.00 | 1.00 | 1.00 | 1.00 | 1.00 | 1.00 |
| Urea | 1.00 | 1.00 | 1.00 | 1.00 | 1.00 | 1.00 |
| Squalene | 1.28 | 1.28 | 1.28 | 1.28 | 1.28 | 1.28 |
| Cetyl Dimethicone | 1.00 | 1.00 | 1.00 | 1.00 | 1.00 | 1.00 |
| Silicone Fluid 344 | 0.70 | 0.70 | 0.70 | 0.70 | 0.70 | 0.70 |
| Cetyl Dimethicone Copolyol | 0.30 | 0.30 | 0.30 | 0.30 | 0.30 | 0.30 |
| Chitosan Lactate | 0.20 | 0.20 | 0.20 | 0.20 | 0.20 | 0.20 |
| Tocopheryl Acetate | 0.20 | 0.20 | 0.20 | 0.20 | 0.20 | 0.20 |
| Glycine | 0.50 | 0.50 | 0.50 | 0.50 | 0.50 | 0.50 |
| Sodium PCA | 0.50 | 0.50 | 0.50 | 0.50 | 0.50 | 0.50 |
| Glydant Plus ® | 0.10 | 0.10 | 0.10 | 0.10 | 0.10 | 0.10 |
| Disodium EDTA | 0.10 | 0.10 | 0.10 | 0.10 | 0.10 | 0.10 |
| Plant Pseudocollagen | 0.10 | 0.10 | 0.10 | 0.10 | 0.10 | 0.10 |
| Colorant | 0.10 | 0.10 | 0.10 | 0.10 | 0.10 | 0.10 |
| Ceramide I and III | 0.07 | 0.07 | 0.07 | 0.07 | 0.07 | 0.07 |
| Hydroxycaprylic Acid | 0.05 | 0.05 | 0.05 | 0.05 | 0.05 | 0.05 |
| Ascorbyl Palmitate | 0.02 | 0.020 | 0.20 | 0.20 | 0.20 | 0.20 |
| Beta Glucan | 0.01 | 0.01 | 0.01 | 0.01 | 0.01 | 0.01 |
| L-Serine | 0.01 | 0.01 | 0.01 | 0.01 | 0.01 | 0.01 |
| Water | to 100 | to 100 | to 100 | to 100 | to 100 | to 100 |

*Contains 22.5% Parsol MCX ®, 10% Dow Corning 3225C; Phenoxyethanol; Paraben; Phospholipid and the balance water.
**Cetyl Octanoate/Aluminum Distearate

EXAMPLE 3

A further set of experiments were conducted to evaluate the SPF contribution from sunscreen agents both outside and within a microfluidized medium. Table V sets forth the base composition of a fully formulated product, except without sunscreen. Test protocol was identical to that described under Example 1.

TABLE V

| BASE COMPOSITION | |
|---|---|
| COMPONENTS | WEIGHT % |
| Dow Corning 3225C ® | 14.00 |
| Aluminum Stearate Gel | 5.00 |
| Glycerin | 3.00 |
| Sodium Chloride | 3.00 |
| Butylene Glycol | 2.00 |
| Squalene | 1.28 |
| Actiglide J ® | 1.50 |
| Cetyl Dimethicone | 1.00 |
| Urea | 1.00 |
| Sodium Lactate Solution | 1.00 |
| Glycine | 0.50 |
| Sodium PCA | 0.50 |
| Chitosan Lactate | 0.20 |
| Tocopheryl Acetate | 0.20 |
| Cetyl Dimethicone Copolyol | 0.20 |
| Glydant Plus ® | 0.10 |
| Disodium EDTA | 0.10 |
| Plant Pseudocollagen | 0.10 |
| 0.5% FD&C Red #4 | 0.08 |
| Ceramide | 0.07 |
| Fragrance | 0.05 |
| Hydroxycaprylic Acid | 0.05 |
| Colorant | 0.40 |
| Ascorbyl Palmitate | 0.02 |
| Beta Glucan | 0.01 |
| L-Serine | 0.01 |
| Silicone Fluid 344 | 0–0.7 |
| Deionized Water | to 100 |

TABLE VI

| SUNSCREEN COMPONENTS | A | B | C | D | E | F |
|---|---|---|---|---|---|---|
| Parsol MCX (within Base Emulsion but external of Microfluidized Medium) | 0 | 0 | 0 | 5.0 | 6.0 | 3.0 |
| Parsol MCX (within Microfluidized Medium) | 0 | 2.0 | 4.0 | 0 | 0 | 2.0 |
| None (Base Emulsion) | 100 | 98.0 | 96.0 | 95.5 | 94.0 | 95.0 |

TABLE VII

| SUNSCREEN ACTIVITY | A | B | C | D | E | F |
|---|---|---|---|---|---|---|
| SPF | 1.0 | 7.3 | 8.7 | 12.7 | 15.8 | 16.9 |

From Table VII it is evident that Parsol MCX® when distributed between both the oil and water phases as in Formula F exhibited the highest SPF. Formula D which had a higher amount of Parsol MCX® (6%) than that of Formula F nevertheless exhibited a lower SPF than the latter composition. From these results it is again seen that the combination of sunscreen agent having a portion within the base emulsion and another portion within the microfluidized medium can result in an overall composition of higher than expected SPF value.

The foregoing description and Examples illustrate selected embodiments on the present invention. In light thereof, various modifications will be suggested to one skilled in the art, all of which are within the spirit and purview of this invention.

What is claimed is:

1. A sunscreen composition comprising:

(i) from about 1 to about 90% by weight of water;

(ii) from about 1 to about 90% by weight of an emollient oil;

(iii) from about 0.1 to about 30% by weight of an organic sunscreen agent with a chromophoric group active within the ultraviolet radiation range from 290 to 400 nm; and (iv) from about 0.1 to about 50% by weight of a microfluidized medium comprising:

from about 1 to about 80% by weight of water;

from about 0.001 to about 5% by weight of a phospholipid;

from about 1 to about 50% by weight of an organic sunscreen agent identical to that of component (iii), and the medium being formulated and microfluidized prior to blending with components (i) to (iii).

2. A composition according to claim 1 wherein the organic sunscreen agent is selected from the group consisting of benzophenone-3, benzophenone-4, benzophenone-6, benzophenone-8, benzophenone-12, butyl methoxy dibenzoyl methane, PABA, octyl dimethyl PABA, octyl methoxycinnamate and combinations thereof.

3. A composition according to claim 2 wherein the organic sunscreen agent is octyl methoxycinnamate.

4. A composition according to claim 1 wherein the emollient oil present in highest concentration is cyclomethicone, dimethicone copolyol and mixtures thereof.

5. A composition according to claim 1 wherein the microfluidized medium further comprises from about 1 to about 30% by weight of a silicone oil.

6. A composition according to claim 5 wherein the silicone oil of the microfluidized medium is selected from the group consisting of cyclomethicone, dimethicone copolyol and mixtures thereof.

* * * * *

UNITED STATES PATENT AND TRADEMARK OFFICE
CERTIFICATE OF CORRECTION

PATENT NO. : 5,486,352
DATED : January 23, 1996
INVENTOR(S) : Guerrero

It is certified that error appears in the above-indentified patent and that said Letters Patent is hereby corrected as shown below:

On the title page:
In the Assignee Section "Elizabeth Arden Company," should read -- Elizabeth Arden Company, Division of Conopco, Inc. --.

Signed and Sealed this

Fourteenth Day of May, 1996

Attest:

BRUCE LEHMAN

*Attesting Officer*     *Commissioner of Patents and Trademarks*